United States Patent
Minami et al.

[11] Patent Number: 6,040,612
[45] Date of Patent: Mar. 21, 2000

[54] IMAGE PICKUP APPARATUS FOR ENDOSCOPE HAVING REDUCED DIAMETER

[75] Inventors: Itsuji Minami; Kazuaki Takahashi, both of Omiya, Japan

[73] Assignee: Fuji Photo Optical Co., Ltd., Saitama, Japan

[21] Appl. No.: 09/013,934

[22] Filed: Jan. 27, 1998

[30] Foreign Application Priority Data

Feb. 7, 1997 [JP] Japan .................................. 9-039936

[51] Int. Cl.⁷ .............................................. H01L 31/0232
[52] U.S. Cl. .......................... 257/432; 257/433; 257/774; 257/696; 257/698
[58] Field of Search ............................. 257/692, 693, 257/696, 698, 774, 432, 433

[56] References Cited

U.S. PATENT DOCUMENTS 5,909,054  6/1999  Kozono ................................. 257/667

Primary Examiner—Minh Loan Tran
Attorney, Agent, or Firm—Snider & Associates; Ronald R. Snider

[57] ABSTRACT

An image pickup apparatus or method of the present invention decreases the diameter of an image pickup device assembly by decreasing the thickness of the assembly. A conductor lead (inner lead of TAB product) is formed on a terminal of a CCD so as to protrude from the outer periphery of the main frame of an image pickup device body in accordance with the TAB (Tape Automated Bonding) method capable of realizing mass production, a cover glass is set so that an air gap is formed between the CCD and its image pickup plane side, and thereby an image pickup device body is formed. Moreover, the image pickup device body is set to an aperture of a circuit board to connect the conductor lead to a terminal at the circuit board side. Thereby, it is unnecessary to use a conventional box-type package for storing the CCD.

4 Claims, 5 Drawing Sheets

IMAGE PICKUP APPARATUS FOR ENDOSCOPE HAVING REDUCED DIAMETER

BACKGROUND OF THE INVENTION

This application claims the priority of Japanese Patent Application No. 9-39936 filed on Feb. 7, 1997, which is incorporated herein by reference.

1. Field of the Invention

The present invention relates to an image pickup apparatus for an endoscope, particularly to a structure and a fabrication method of an image pickup apparatus to be mounted on a circuit board by making at least the image pickup plane side of a solid-state image pickup device airtight.

2. Description of the Prior Art

FIGS. 8(A) and 8(B) show an assembly constituted by setting a solid-state image pickup device into a package in a conventional electronic endoscope and the assembly is used for a simultaneous endoscope. As shown in FIG. 8, a CCD (Charge Coupled Device) 1 serving as a solid-state image pickup device is stored in a box-type package (also serving as a circuit board) 2 made of ceramic or the like and a terminal G of the CCD 1 side and a terminal (pad) H of the package-2 side are connected by a bonding wire 3.

Moreover, a cover glass 4 with an air gap provided for the image pickup plane side (upper side) of the CCD 1 is bonded onto the package 2 and the package 2 is made airtight. That is, in the case of the CCD 1, a microlens and a color filter are formed on the image pickup plane, the function of the microlens is held by the air gap, and the color filter is prevented from deteriorating by the airtight state.

A terminal (pad) I connected to the terminal H is formed at the left end of the package 2 in FIG. 8(A) and a signal cable is connected to the terminal I. Thereby, it is possible to transmit a driving signal supplied to the CCD 1 and a video signal read from the CCD 1.

FIG. 9 shows the inside of the front end of an endoscope with the image pickup device assembly in FIG. 8 set in it. At the front end 5, an objective optical system 6 is set onto the cover glass 4 of the package 2 through a prism. A light guide 7 is set to the right and left of the objective optical system 6 and an action-tool passing channel 8 or the like is formed below the package 2. According to the above structure, the inside of an object to be observed is picked up by imaging the object captured by the objective optical system 6 on the pickup plane of the CCD 1.

BRIEF SUMMARY OF THE INVENTION

Object of the Invention

However, a conventional image pickup apparatus for an endoscope has a problem that the diameter of the endoscope cannot be decreased because the CCD 1 is stored in the package 2 as described above. That is, as shown in FIG. 8, a thickness (longitudinal length) L1 determined by the package 2 and cover glass 4 influences the longitudinal diameter of the front end 5. By decreasing the thickness L1, however, it is possible to decrease the diameter of the endoscope.

SUMMARY OF THE INVENTION

The present invention is made to solve the above problem and its object is to provide an image pickup apparatus for an endoscope capable of decreasing the diameter of an image pickup device by decreasing the thickness of an image pickup device assembly and moreover, capable of decreasing the fabrication cost by using an image pickup device product obtained through the TAB system.

To achieve the above object, an image pickup apparatus for an endoscope of the present invention is characterized by forming a conductor lead connected to a terminal at the image pickup plane side of an image pickup device and protruded from the outer periphery of the image pickup device, using an image pickup device body in which an optical element (cover glass) is bonded to the image pickup plane side of the image pickup device by a sealant so that an air gap is formed between the image pickup device and its image pickup plane and a circuit board on which an aperture for dropping at least the main frame of the image pickup device body is formed, setting the main frame of the image pickup device body onto the aperture, and connecting the conductor lead to a terminal of the circuit board.

As the above image pickup device body, it is preferable to use an image pickup device body obtained by separating an inner lead and an outer lead of a conductor from a tape-like product fabricated while provided with the inner lead and outer lead by the tape automated bonding method.

Moreover, it is preferable to separate the inner lead from the tape-like product by slightly leaving the tape portion of the non-connection end of the inner lead.

Moreover, it is possible to connect the image pickup device body by folding the conductor lead, forming a through-hole electrode on the circuit board, and inserting the conductor lead into the through-hole electrode.

A fabrication method of an image pickup apparatus for an endoscope of other invention is characterized by connecting an image pickup device body to a terminal at the image pickup plane side of an image pickup device and forming a conductor lead so as to protrude from the outer periphery of the image pickup device, forming an air gap to be an airtight state between the image pickup device and its image pickup plane and bonding an optical element to the image pickup plane side of the image pickup device by a sealant, forming at least an aperture for dropping the image pickup device body on a circuit board, setting the main frame of the image pickup device body to the aperture and connecting the conductor lead to a terminal of the circuit board.

According to the above structure, an air gap is formed on the image pickup plane of a solid-state image pickup device by bonding a glass cover by a sealant and an airtight state is maintained. Therefore, it is not necessary to use a conventional box-type package and thereby, it is possible to decrease the thickness of an image pickup device assembly.

Moreover, by connecting a conductor lead by the above tape automated bonding method, forming an image pickup device body by bonding a glass cover to the upper side of a solid-state image pickup device, and separating the image pickup device body by the inner lead which is the conductor lead, it is possible to easily fabricate an image pickup apparatus for an endoscope by applying the image pickup device body obtained by the tape automated bonding method to a circuit board. In this case, by separating the image pickup device body from a tape while slightly leaving the tape portion at an end of the inner lead, the inner lead is not divided into pieces and thus, connection to the circuit board is preferably performed.

DETAILED DESCRIPTION OF THE PREFERRED EMBODIMENTS

Figure 7:
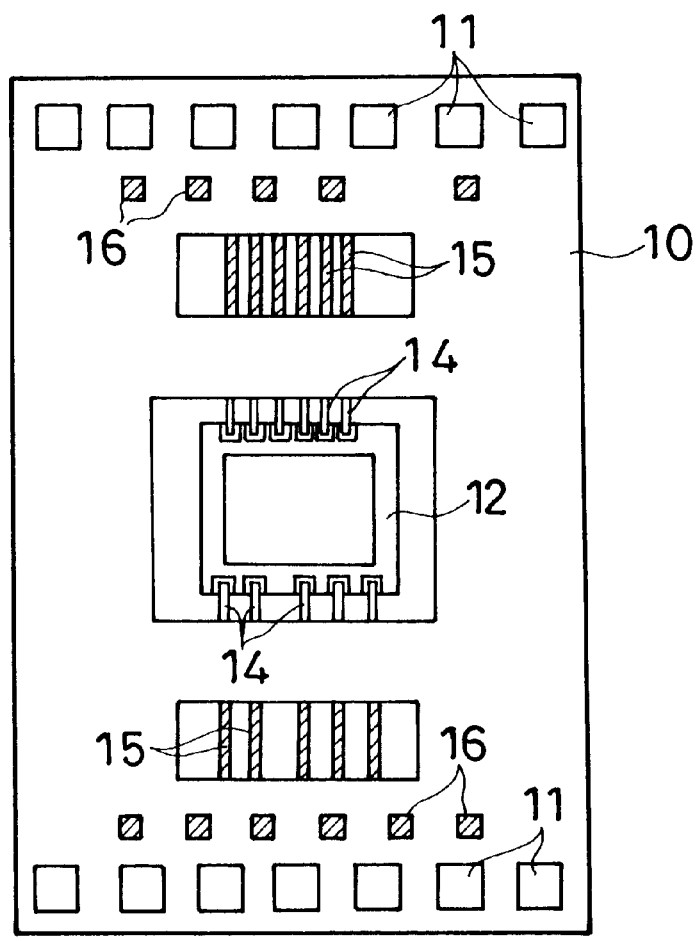
FIG. 7 is a top view showing the structure of a product according to the TAB method.
Figure 8A:
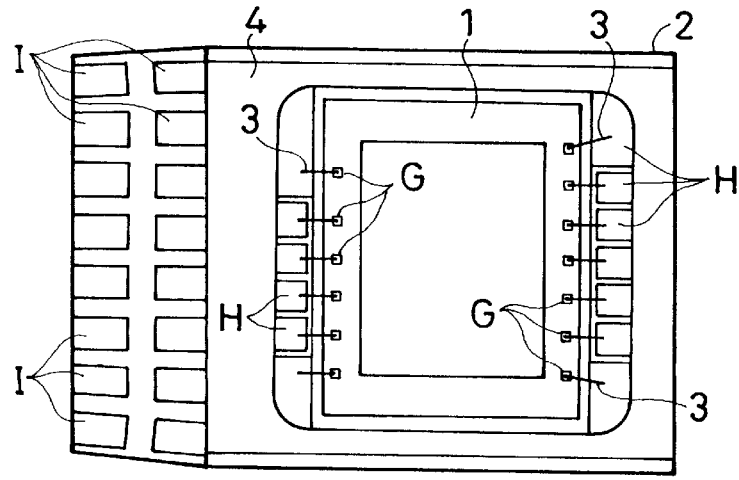
FIG. 8(A) is a top view showing the structure of a conventional image pickup device assembly.
Figure 8B:
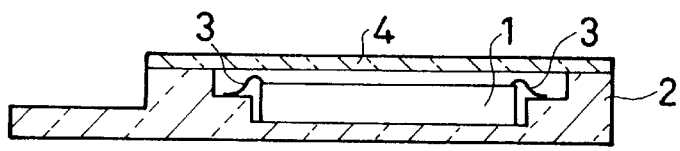
FIG. 8(B) is a side of the assembly in FIG. 8(A)

FIG. 7 shows the structure of a product according to the tape automated bonding (TAB) method. First, the product is described below. That is, a CCD serving as a solid-state image pickup device is used for a video camera and the like. Connection with the CCD is performed by a mass production system in accordance with the TAB method. When the CCD product fabricated by a mass production system can be used as an image pickup device for an endoscope, it is possible to reduce costs.

In FIG. 7, in the case of the TAB method, a flexible tape 10 is provided with a sprocket hole 11 and a CCD 12 set to a central hole is connected with a conductor lead while carrying is performed by the sprocket hole 11. That is, an inner lead (conductor lead) 14 is connected to the illustrated CCD 12 and an outer lead (conductor lead) 15 and a test pad 16 are formed by being connected to the inner lead 14. The inner lead 14, outer lead 15, and test pad 16 are connected by the lower side of the tape 10 or the like.

Moreover, a product by the tape 10 is finally inspected on its connection state and the like by the test pad 16 and the fabrication is completed. Moreover, to connect the product to a circuit board or the like, the sprocket hole 11 and test pad 16 are separated from the tape 10 and the outer lead 15 is used as a lead for connection to other circuit board (OLB—Outer Lead Bonding).

According to the above TAB method, formation, connection, and inspection of the CCD 12 and conductor leads 14 and 15 are performed by a mass production system. When an image pickup device product obtained by the method can be used for an endoscope, it is possible to fabricate an image pickup apparatus for an endoscope at a low cost.

First embodiment

Figure 1A:
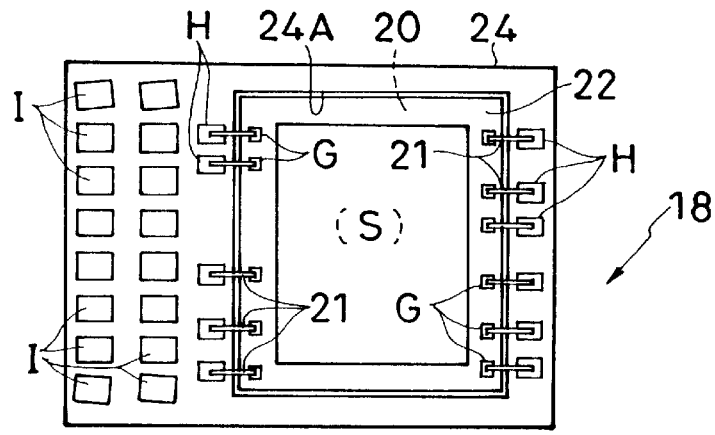
FIG. 1(A) is a top view of the structure of the image pickup apparatus for an endoscope of the first embodiment of the present invention, showing a state of setting an image pickup device body to a circuit board.
Figure 1B:
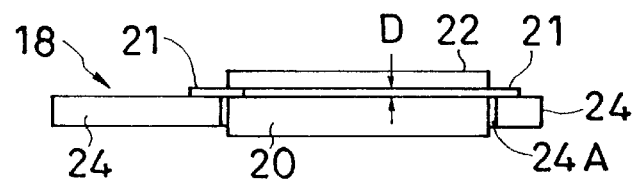
FIG. 1(B) is a side view of FIG. 1(A)
Figure 1C:
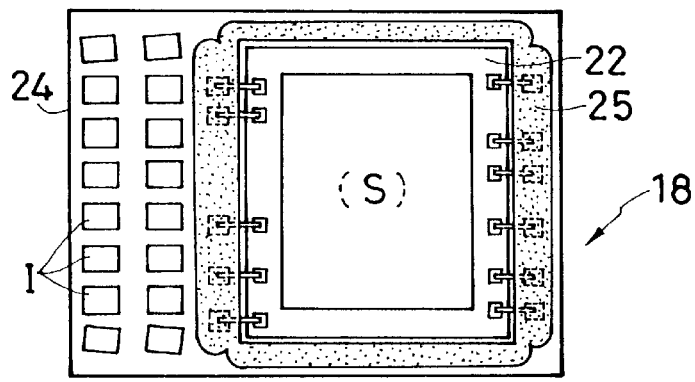
FIG. 1(C) is a top view of FIG. 1(A) showing a state of applying an adhesive to the assembly in FIG. 1(A)
Figure 1D:
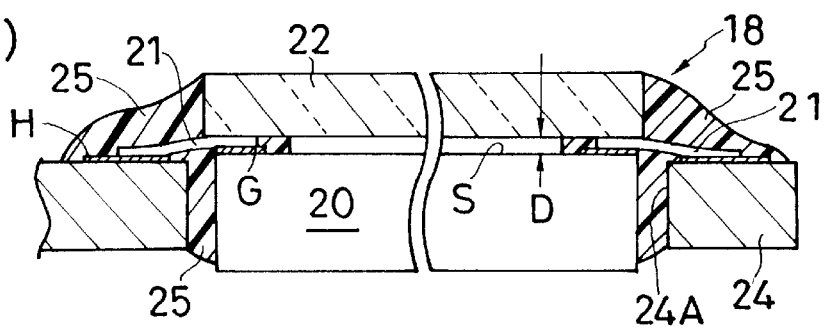
FIG. 1(D) is a locally enlarged view of the side of FIG. 1(C)
Figure 2:
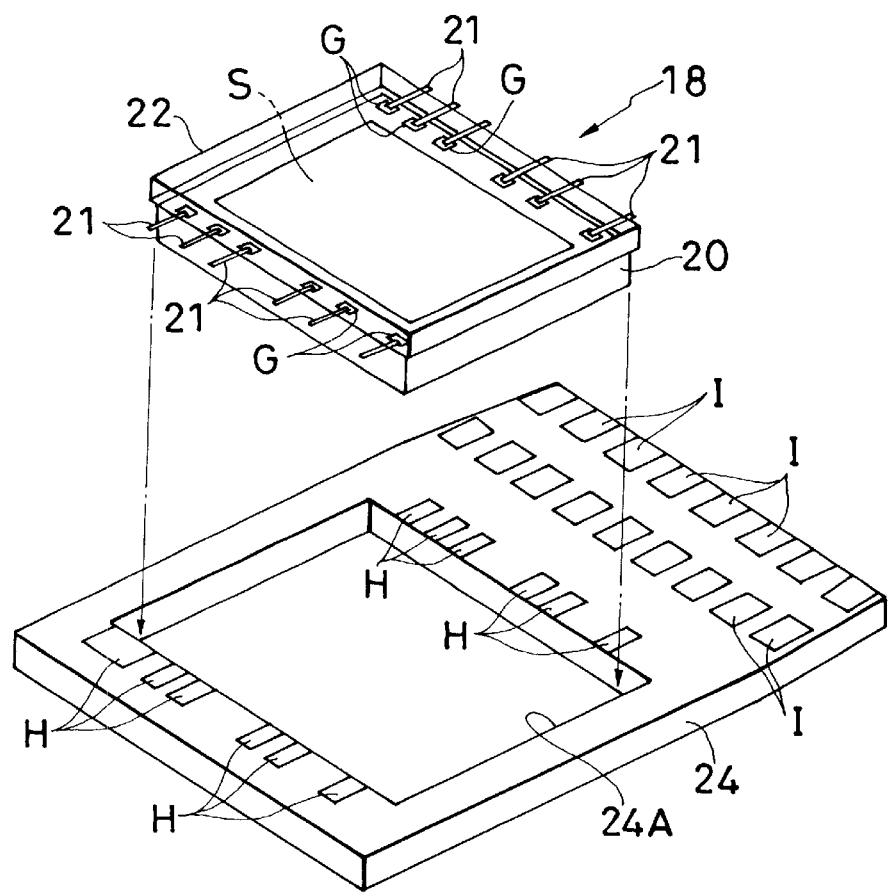
FIG. 2 is an exploded perspective view of the image pickup device body and circuit board in FIG. 1.
Figure 3:
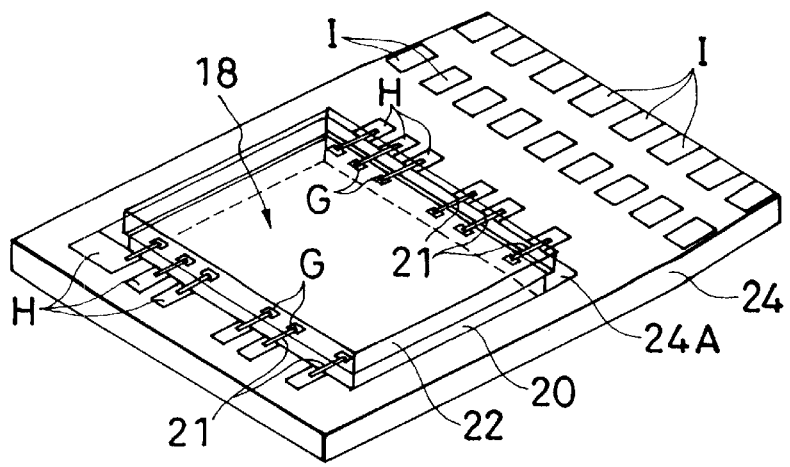
FIG. 3 is a perspective view showing a state of combining the image pickup device body and circuit board in FIG. 2.

FIGS. 1 to 4 show the structure of the image pickup apparatus for an endoscope of the first embodiment of the present invention, in which a cover glass is shown in a perspective state. FIGS. 1(A) and 1(B) and FIG. 3 show states of connecting an image pickup device body to a circuit board and FIG. 2 shows a state before setting an image pickup device body to a circuit board. In FIG. 2, a thin flat conductor lead (inner lead) 21 is contact-bonded (bump-connected) to a terminal G set to the image pickup plane S side of a CCD 20 and a cover glass 22 is bonded to the image pickup device plane S by a sealant and thus, an image pickup device body 18 is formed. This image pickup device body 18 is fabricated in accordance with the TAB (Tape Automated Bonding) method.

That is, as shown in FIG. 7, the inner lead (14) and outer lead (15) serving as the conductor lead 21 are formed on and connected to a CCD set to the central hole of a carrying tape (10) serving as an insulating member and thereafter, the cover glass 22 is bonded by a sealant such as an adhesive as shown in FIG. 1(B). In this case, an air gap of approx. 50 $\mu$m is formed between the cover glass 22 and the image pickup plane S in accordance with the thickness of the conductor lead 21 and presence of the sealant and the airtightness of the air gap portion is maintained by uniformly injecting a sealant to the outer boundary except the substantial image pickup region (effective pixel region) of the image pickup plane S.

Moreover, in the case of the product by the tape, the outer lead (15) is not used as a conductor lead for connection but the inner lead (14) is used as a connection lead. Therefore, the tape is cut at the non-connection end (end not connected to the CCD 2) of the inner lead (14) to separate the image pickup device body 18 from the tape. According to the above inner lead (14), decrease of the front end diameter is accelerated compared to the case of using an outer lead (OLB method).

Moreover, as shown in FIG. 2, an aperture (through-hole) 24A through which the CCD 20 can be inserted is formed on a circuit board 24 and a terminal H for connecting the conductor lead 21 is provided for the front and rear margins of the aperture 24A, and a terminal I for connecting a signal cable is provided for the rear end. The terminals I and H are connected by a wiring pattern (not illustrated) formed on the upper and lower sides of the board.

Then, the image pickup device body 18 is set and connected to the circuit board 24 and the state shown in FIGS. 1(A), 1(B) and FIG. 3 is realized. That is, the portion of the CCD 20 of the image pickup device body 18 is set to the aperture 24A of the circuit board 24 and the conductor lead 21 is contact-bonded (bump-connected) to the terminal H. Thereafter, an adhesive 25 (any other filler can be also used) is injected into the gap between the entire outer periphery of the CCD 20 and the aperture 24A and thereby, the image pickup device body 18 is firmly fixed to the circuit board 24.

Moreover, in the case of this embodiment, the adhesive 25 is applied to the entire outer periphery of the cover glass 22 as shown in FIGS. 1(C) and 1(D) and thereby, advantages can be obtained that the image pickup device body 18 is strongly fixed to the circuit board 24 and the airtightness of the air gap between the image pickup plane S of the CCD 20 and the cover glass 22 can be completely secured.

Figure 4:
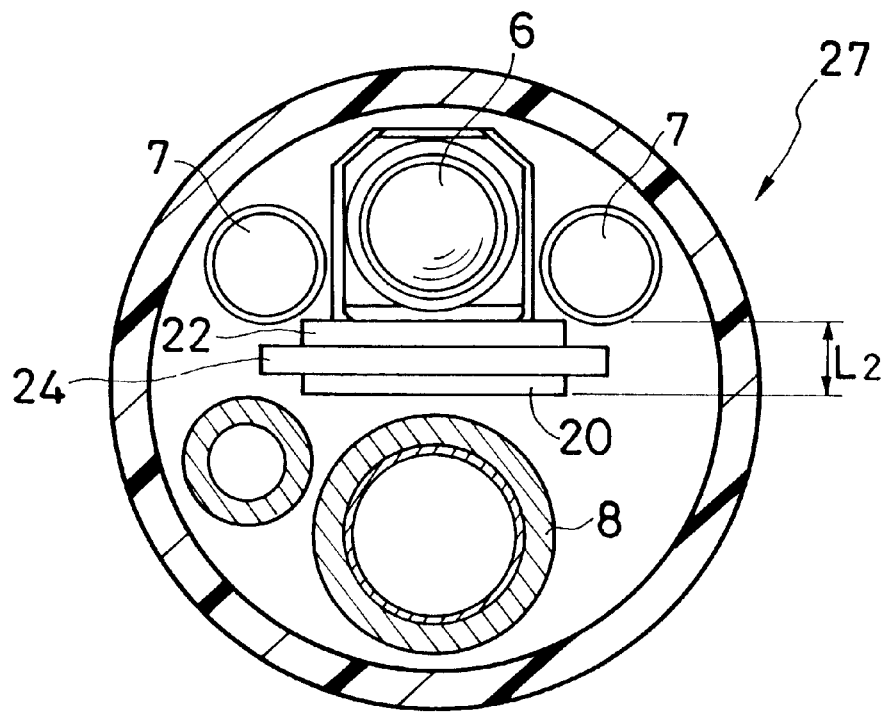
FIG. 4 is an illustration showing a state of setting the image pickup device assembly of the first embodiment to the front end of an endoscope.
Figure 9:
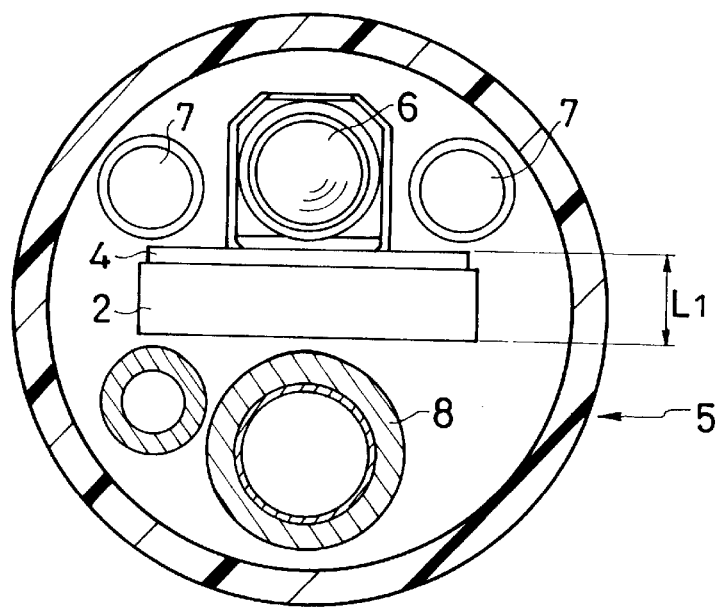
FIG. 9 is an illustration showing a state of setting the image pickup device assembly in FIG. 7 to an endoscope.

FIG. 4 shows a layout drawing of an image pickup device assembly in the front end of an endoscope corresponding to the prior art in FIG. 9. Also at the front end 27 of this embodiment, the objective optical system 6 is set onto the cover glass 22 through a prism and the light guide 7 and the action-tool passing channel 8 are arranged there. By comparing FIG. 4 with FIG. 9, it is found that the thickness L2 of the image pickup device assembly of this embodiment is not influenced by the thickness of the circuit board 24 and it is substantially equal to the sum of the thickness of the CCD 20 and that of the cover glass 22 and resultingly, it is smaller than the conventional thickness L1. Therefore, the diameter of the front end 27 is smaller than that of the conventional front end 5.

Second embodiment

Figure 5:
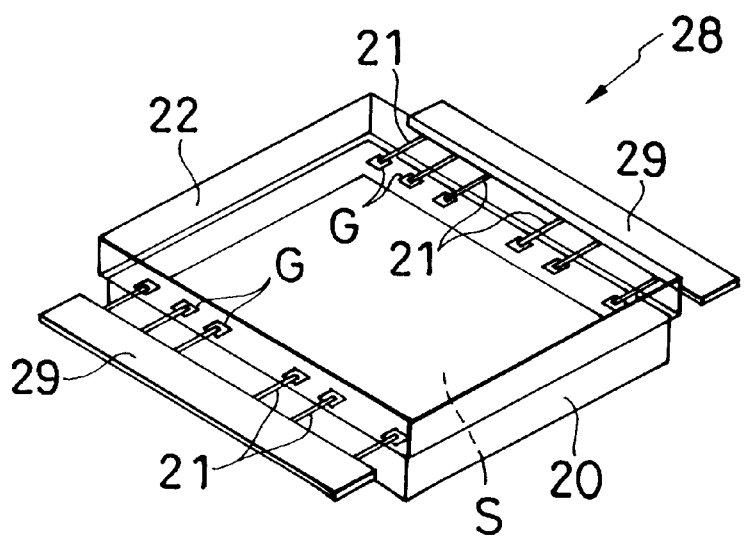
FIG. 5 is a perspective view showing the structure of the image pickup device body of the second embodiment.

FIG. 5 shows the structure of the second embodiment. In the case of this embodiment, a part of a tape at fabrication is left on the conductor lead of an image pickup device body. That is, in the case of the image pickup device body 28 in FIG. 5, the conductor lead (inner lead) 21 is formed on the upper-side terminal G of the CCD 20 by the TAB method similarly to the case of the first embodiment and moreover, an air gap is formed on the image pickup plane S to bond the cover glass 22. Then, finally, when separating the conductor lead 21 serving as an inner lead from the tape (FIG. 7), a part of the tape is left as an auxiliary tape 29.

This auxiliary tape 29 has the advantages that the alignment state of the thin flat conductor lead 21 is not disordered, the image pickup device body 28 is easily handled, and moreover, the circuit board 24 is preferably connected to a terminal.

Third embodiment

Figure 6:
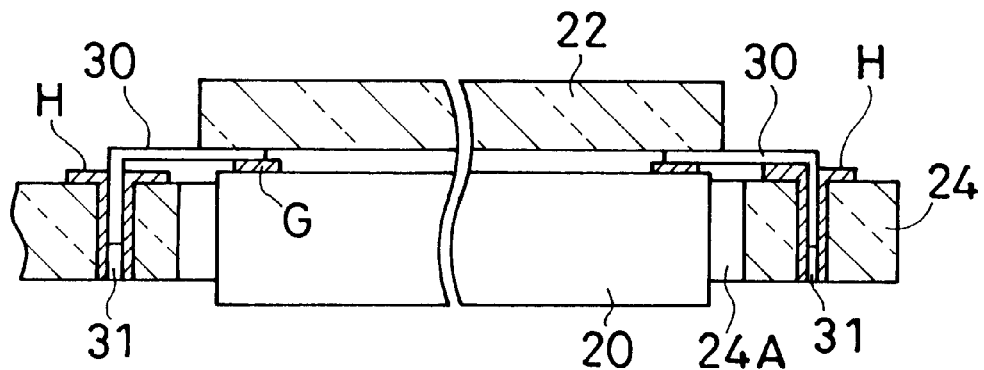
FIG. 6 is a sectional view showing the structure of the image pickup device assembly of the third embodiment.

FIG. 6 shows the structure of the third embodiment. As shown in FIG. 6, in the case of the third embodiment, a conductor lead 30 connected to the terminal G of the CCD 20 is bent downward as illustrated. Moreover, a through-hole 31 is simultaneously formed on the portion of the terminal H of the circuit board 24 so as to connect the conductor lead 30 with the through-hole 31 by inserting the lead 30 into the through hole 31.

Also according to the above connection between the conductor lead 30 with the through-hole 31, the CCD 20 can be electrically connected with the circuit board 24 and thus, it is possible to obtain the advantage same as that of the first embodiment.

As described above, according to the present invention, a conventional box-type package is unnecessary, the thickness of an image pickup device body can be decreased, and the diameter of an endoscope can be decreased. Moreover, by using an image pickup device body mass-produced in accordance with the TAB method, it is possible to decrease the cost of an endoscope. Moreover, by keeping a conductor lead in an aligned state by an auxiliary tape slightly leaving the tape portion, the advantages can be obtained that an image pickup device body is easily handled and moreover, preferably connected to a circuit board.

What is claimed is:

1. An image pickup apparatus for an endoscope comprising:

a circuit board having a through hole aperture and at least one terminal;

an image pickup device body having at least one terminal on an image plane pickup side, and an outer periphery;

a conductor lead connected to the terminal of the image pickup device and protruding from the outer periphery;

an optical element attached to the image plane pickup side of the image pickup device body by a sealant;

an airtight air gap formed between the image pickup device, image pickup plane and the optical element;

wherein the image pickup device body is inside the circuit board through hole aperture; and wherein the conductor lead is a tape automated bond lead.

2. The image pickup apparatus in accordance with claim 1 wherein a bottom portion of the image pickup device extends downward through the through hole aperture and beyond a bottom plane of the circuit board.

3. The image pickup apparatus for an endoscope according to claim 1, wherein said image pickup device body is connected to the circuit board by bending the conductor lead and inserting the conductor lead into a through-hole electrode in said circuit board.

4. The image pickup apparatus in accordance with claim 1 wherein the tape automated bond lead lies on a surface of the image pickup body which permits a distance D to be controlled by the thickness of the sealant.

* * * * *